United States Patent [19]

Coleman et al.

[11] Patent Number: 5,709,943
[45] Date of Patent: Jan. 20, 1998

[54] BIOLOGICAL ADSORPTION SUPPORTS

[75] Inventors: Patrick L. Coleman, Minneapolis; Mark K. Debe, Stillwater; Julie B. Stahl, St. Paul, all of Minn.

[73] Assignee: Minnesota Mining and Manufacturing Company, St. Paul, Minn.

[21] Appl. No.: 434,930

[22] Filed: May 4, 1995

[51] Int. Cl.[6] .................................................. D02B 3/00
[52] U.S. Cl. ........................... 428/378; 428/379; 428/380
[58] Field of Search ..................................... 428/378, 379, 428/380

[56] References Cited

U.S. PATENT DOCUMENTS 5,388,430  2/1995  Parsonage et al. ...................... 204/412

FOREIGN PATENT DOCUMENTS 56-144085  10/1981  Japan.

Primary Examiner—Edward J. Cain
Attorney, Agent, or Firm—Gary L. Griswold; Walter N. Kirn; Carolyn V. Peters

[57] ABSTRACT

The present invention provides biological assay and adsorption supports comprising an inert substrate supporting a nanostructured surface comprising metal coated, oriented, discrete submicron-size whiskers. Optionally, conformally metal coated whiskers may be partially encapsulated or conformally coated with a second material. The nanostructured surface adsorbs biomolecules rapidly at high levels of tight binding without vortexing or agitation. Advantageously, the bound biomolecules retain their biological activity.

13 Claims, 7 Drawing Sheets

BIOLOGICAL ADSORPTION SUPPORTS

TECHNICAL FIELD

This invention relates to biological adsorption supports, and more particularly to biological adsorption supports based on a nanostructured surface morphology.

BACKGROUND OF THE INVENTION

Conventional biomolecule adsorption supports consist of polymers, copolymers or chemically-functionalized polymer surfaces with no overt physical microstructure, that is, the surface area is defined by the average geometric shape of the support. On a microscale, the polymer surfaces offer a heterogeneous mixture of hydrophobic and hydrophilic sites, producing a range of different levels of affinity of the biomolecule for the sorbent substrate. Above a flat planar surface, the biomolecules diffuse towards and away from the substrate with equal probability. Generally the rate of adsorption is enhanced by vortexing and rocking of the solutions.

SUMMARY OF THE INVENTION

Briefly, in one aspect of the present invention a biological adsorption support is provided comprising an inert substrate supporting a nanostructured surface comprising metal-coated, oriented, discrete submicron-size elements having a high aspect ratio, for example greater than 3 and an areal number density in the range of $1$–$200/\mu m^2$.

Advantageously, the physical morphology of the nanostructured surface, described here as nanostructured because of the nanometer size scale of the surface features, provides high specific surface area within short diffusional path lengths to biomolecules in solutions brought into contact with the surface. The coating material of the nanostructured whiskers onto which the biomolecules adsorb is easily varied, but simple metals such as the noble metals are preferred. The substrate carrying the nanostructured surface is typically flexible, inert and easily cut or formed. Biomolecule adsorption onto the support is rapid, results in high (85–90%) levels of tight binding, produces large absolute binding quantifies ($\sim 10$ $\mu g/cm^2$), and requires no vortexing or agitation. Furthermore, the tightly bound biomolecule is shown to retain its biological activity. Both the binding tightness and retention of biological activity are particularly surprising considering the highly heterogeneous nature of biologically active materials, that is a terpolymer is considered simple (typically only three different monomers) in comparison to biologically active materials (typically having eleven or more different monomers)

Nanostructured surfaces of the present invention have a high aspect ratio, an areal number density, preferably in the range of $40$–$50/\mu m^2$, and can offer 10–15 times the planar surface area for biomolecule adsorption over other art known adsorption support. Pure metal coatings, such as Pt on the nanostructured whiskers, produce a uniformly sorbent surface. Furthermore, the large aspect ratio of the oriented elements and their large packing densities (that is, areal number density) may permit temporary entrapment of the biomolecules as they diffuse into the nanostructured layer, allowing multiple opportunities for biomolecule/sorbent surface collisions, without the need for vortexing or rocking.

In another aspect of the present invention, the biological adsorption support can be advantageously used as a separation device, such as a filter, sensor and the like. For example, a fluid stream containing a biologically active material can be passed over or through the biological adsorption support such that one or more biologically active materials in the fluid stream will be extracted or separated from the fluid. The extracted or separated biologically active material adheres to the nanostructure elements as a monolayer. Biologically active material can be removed in such a fashion to any arbitrary end-point, for example until a predetermined level of material is adsorbed, for a predetermined period of time, or until the support is saturated with biologically active material.

In yet another aspect of the present invention, the biological adsorption supports can be used in a steady-state biological process for conversion of one species to another, for example, as a catalyst. These characteristics provide several aspects of this invention, which would not be expected by those skilled in the art. As compared to what is known in the adsorption support art, the rate of binding of biomolecules onto the surface of this material is rapid, much faster than that observed with biomolecule binding to conventional planar surfaces. Surprisingly, biomolecules bind both rapidly and with a high surface coverage.

Another advantageous characteristic of the present invention is the tightness of biomolecule binding as illustrated by its resistance to desorption upon treatment with sodium dodecylsulfate (SDS). Such high residual binding is generally only observed with covalent coupling of such biomolecules to a surface. It is also surprising that such tenacious binding can be present simultaneously with retention of biological activity.

Taking advantage of the particular characteristics of the nanostructure elements, a composite article can be made comprising (a) a biological adsorption support, comprised of an inert substrate supporting a nanostructured surface comprising metal-coated, oriented, discrete submicron-size elements having a high aspect ratio and an areal number density in the range of $1$–$200/\mu m^2$ and (b) a monolayer of biologically active material adhered to the metal-coated elements, wherein the adhered layer is biologically active.

Advantageously, the composite article can also be used as a separative device, wherein the biologically active material adhered onto the metal coated elements is specific to a particular biologically active material.

Alternatively, in yet another aspect of the present invention a composite article is provided comprising:

(a) a biological adsorption support, comprised of an inert substrate supporting a nanostructured surface comprising biomolecule absorbent conformal-coated, oriented, discrete submicron-size elements having a high aspect ratio and an areal number density in the range of $1$–$200/\mu m^2$.

(b) a first monolayer of biologically active material adhered to the biomolecule adsorbent conformal-coated elements, wherein the adhered layer is biologically active, and (c) a second monolayer of biologically active material adhered to the first monolayer of biologically active material.

For example, the first composite article could be coated with a first monolayer of biologically active material that will bind, either temporarily or permanently, a pharmaceutical (the second monolayer of biologically active material), such that the pharmaceutical can be coated onto the composite article, either to saturation or to a predetermined dose. This pharmaceutical-coated composite can then be used in such a fashion as to permit timed desorption of the pharmaceutical or sustained retention of a pharmaceutical in a given location that would traditionally be adsorbed or transported away from the area of interest.

In this application:

"biologically active materials" also referred to as "biomolecules" means molecules that are, for instance, biochemically, immunochemically, physiologically, and/or pharmaceutically active, that is, capable of reacting in a manner that affects biological processes and such materials include proteins, antibodies, antigens, enzymes, cofactors, lecithins, hormones, lipids, mediators, receptors, coagulation factors, histones, cell receptors, and cell surface antigens, and further, such materials or biomolecules have molecular weights (as determined by SDS-gel electrophoresis) of at least 1000 and above, and preferably at least 5000 and above.

Description of the Preferred Embodiment(s)

The present invention provides biological adsorption supports comprising an inert substrate supporting a nanostructured surface comprising metal coated, oriented, discrete submicron-size whiskers. Optionally, conformally metal coated whiskers may be partially encapsulated or conformally coated with a second material. The nanostructured surface adsorbs biomolecules rapidly at high levels of tight binding without vortexing or agitation. Advantageously, the bound biomolecules retain their biological activity.

"Nanostructured" as used in this application means the surface region contains a compositional inhomogeneity with a spatial scale on the order of tens of nanometers in at least one dimension. An example of such a nanostructured surface region with a spatial inhomogeneity in two dimensions is one comprised of elongated metal coated elements (nanostructured elements) uniformly oriented on the surface of the substrate, without touching each other, with sufficient numbers per unit area to achieve the desired properties, such as rapid and tight binding. A two-dimensional spatially inhomogeneous nanostructured surface region can be one such that translating through the region along any two of three orthogonal directions, at least two different materials will be observed, for example, the nanostructured elements and voids. Such nanostructured materials have been described, for example U.S. Pat. No. 4,812,352 and such description is incorporated herein by reference.

Figure 1A:
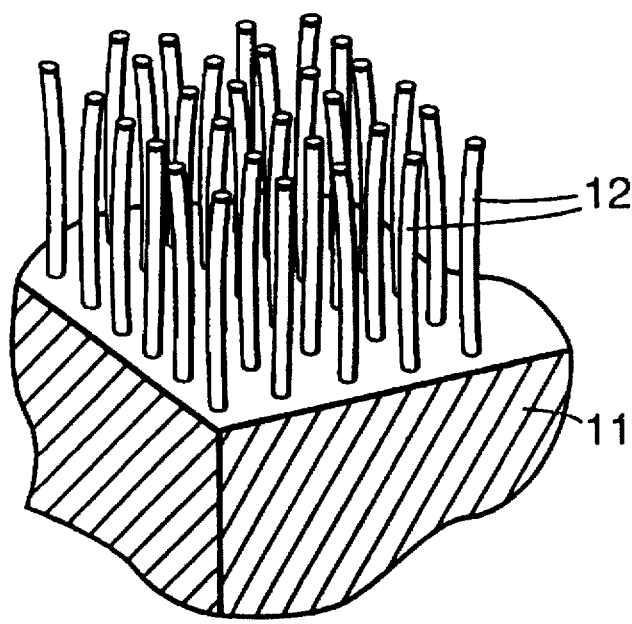
FIG. 1A is a perspective view of uncoated discrete submicron-size whiskers supported by a substrate.
Figure 1B:
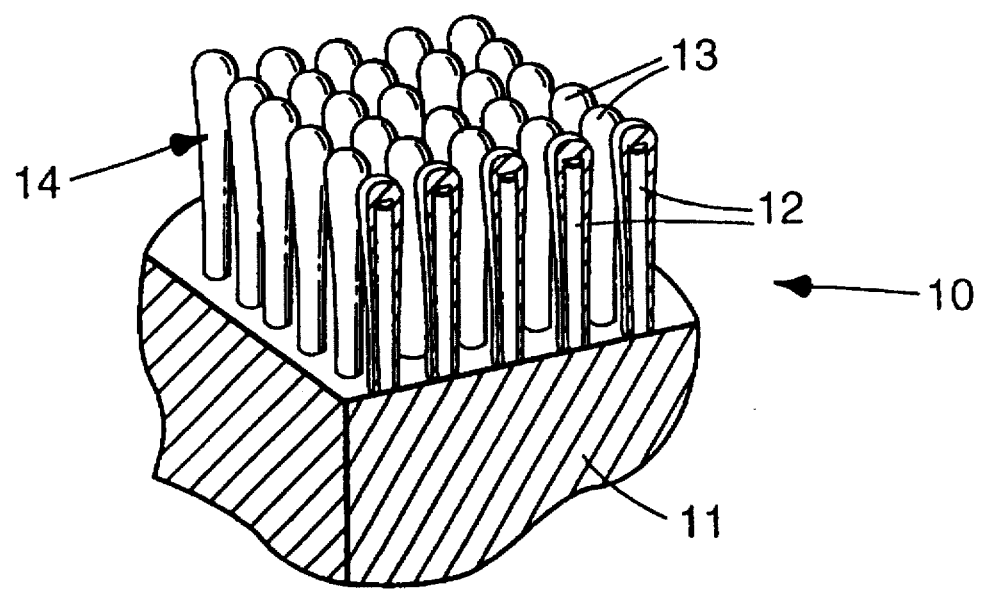
FIG. 1B is a perspective view of FIG. 1A after the discrete submicron-size whiskers have been conformally coated.

Briefly, an organic material having substantially planar shaped molecules and delocalized π-electron density, such as the pigment N,N'-di(3,5-xylyl)perylene-3,4:9,10 bis (dicarboximide), hereafter referred to as PR 149, is vacuum vapor-deposited onto a flexible substrate such as a polyimide web, near room temperature, to a thickness on the order of 0.15 micrometers. Thereafter, the substrate and PR 149 coating is annealed in a vacuum sufficient to cause the initially uniform pigment film to convert to highly nanostructured whiskers. Referring to FIGS. 1(a) and 1(b) the nanostructured surface (10) consists of discrete, uniformly oriented, crystalline whiskers (12), 1 to 2 micrometers tall, with high aspect (length to width) ratios, large areal number densities (1–200/$\mu m^2$), diameters approximately 0.05 micrometers and whisker-to-whisker spacings on the order of 0.05 micrometers or less supported by a substrate (11). The resulting geometric surface area of the crystalline whiskers (12) thus can increase the planar surface area (10) by a factor of 10 to 15. The crystalline whiskers (12) attached to the original substrate (11) can then be conformally coated with metals, semi-metals, semi-conductors, dielectrics or organic materials. In this application, sputter or vapor deposited metal coatings, especially platinum, are shown to be a desirable surface for direct adsorption of the biomolecules. Metal coating (13) also helps strengthen coated whiskers (14) and maintain their attachment to substrate (11) sufficient to withstand immersion into solutions.

Optionally, the coated nanostructured elements described above may be further conformally coated with an organic material so as to apply a thin conformal coating that has a biological functionality around each nanostructured element. Methods for applying this coming include, for example, self-assembled monolayers.

Further, the nanostructured surface described above may be partially encapsulated by overcoating the whiskered structure (14) with a flowable substance, such as a prepolymer, which only partially fills the voids between the whiskers and which upon curing to a solidified state can be delaminated from the original substrate. When delaminating, the solidified polymer partial-encapsulant pulls the whiskers off the original substrate, producing a textured surface due to the protruding ends of the whiskers. This surface now becomes the biomolecule adsorption surface. Many polymers may be used as an encapsulant, and may be selected to further enhance the biomolecule binding.

Preferred substrate materials include organic or inorganic materials, such as polymers, metals, ceramics, glasses, and semiconductors. The preferred organic substrate is metal-coated polyimide film (commercially available from DuPont Corp. under the trade designation KAPTON™). Additional examples of substrate materials appropriate for the present invention can be found in U.S. Pat. No. 4,812,352 and such description is incorporated herein by reference.

A particularly useful process for making the nanostructured surface region of the biological adsorption support used to demonstrate this invention is described in U.S. Pat. No. 5,238,729 and such description is incorporated herein by reference. The nanostructured elements comprising the nanostructured surface region are described in U.S. Pat. Nos. 5,039,561 and 4,812,352 and such description is incorporated herein by reference.

Other means for generating the nanostructured surface include (1) vacuum deposition of organic pigments onto heated substrates, (2) use of physical vapor transport growth instead of vacuum vapor deposition, (3) vacuum deposition of inorganic materials at high incidence angles, (4) ion or rf sputter etching of polymers, semiconductors or alloys having differential sputtering rates, (5) sputter etching of polymers using microisland masking, (6) photolithography (UV and X-ray), and electron beam lithography, (7) hydrolysis of aluminum to produce boehmite, (8) electrochemical etching of metals and electroplating of roughened metals, (9) photofabrication on photopolymer surfaces, (10) directional solidification and etching of eutectics, and (11) vapor liquid solid (VLS) crystal growth. Any of these methods may be able to produce a nanostructured surface. Several techniques or methods are useful for producing the whisker-like configurations. Methods for making inorganic-, metallic-, or semiconductor-based microstructured-layers or microstructures are described in J. Vac. Sci. Tech. 1983, 1(3), 1398–1402 and U.S. Pat. Nos. 4,812,352, 5,039,561 and 5,238,729.

Starting materials useful in preparing whiskers include organic and inorganic compounds. The whiskers are essentially a non-reactive or passive matrix for subsequent thin metal coating, optional conformal coating and optional encapsulant. Preferred organic materials can be broadly classified as polynuclear aromatic hydrocarbons and heterocyclic aromatic compounds. Particularly useful polynuclear aromatic hydrocarbons include, for example, naphthalenes, phenanthrenes, perylenes, anthracenes, coronenes, and pyrenes. A preferred polynuclear aromatic hydrocarbon is N,N'-di(3,5-xylyl)perylene-3,4:9,10 bis(dicarboximide) (commercially available from Hoechst-Celanese Corp. under the trade designation of "G.I. Pigment Red 149", also referred to as "PR149").

The organic material used to produce whiskers may be coated onto a substrate using well-known techniques in the art for applying a layer of an organic material onto a substrate including but not limited to vacuum evaporation, sputter coating, chemical vapor deposition, spray coating, solution adsorption, Langmuir-Blodgett, or blade coating. Preferably, the organic layer is applied by physical vacuum vapor deposition (i.e., sublimation of the organic material under an applied vacuum). The preferred temperature of the substrate during deposition is dependent on the organic material selected. For PR149, a substrate temperature near room temperature (that is, about 25° C.) is satisfactory.

In the preferred method for generating organic whiskers, the thickness of the deposited organic layer will determine the major dimension of the microstructures that form during an annealing step. This preferred process includes depositing the whisker-generating material at or near room temperature and then elevating the substrate temperature to anneal the whisker generating material in a vacuum below approximately 130 Pascals, and preferably below $10^{-2}$ Pascals. Whiskers are grown on a substrate with the characteristics and process described in U.S. Pat. No. 5,039,561 and such descriptions are incorporated herein by reference. This process for obtaining the whiskers is also described in Example 1 herein below.

An alternative process for generating the whiskers includes depositing a whisker-generating material on a substrate wherein the whisker-generating material and the substrate are at an elevated temperature. Material is vacuum-deposited, at vacuums below approximately 130 Pascals until high aspect ratio randomly-oriented whiskers are obtained. This alternative method is also described in U.S. Pat. No. 5,352,651 and such description is incorporated herein by reference.

In both instances, PR149 is the organic material preferred. The thickness of the PR149 layer, prior to annealing is typically in the range from about 0.05 to about 0.3 µm, preferably in the range of 0.05 to 0.15 µm, and most preferably in the range of 0.1 to 0.15 µm. When the organic materials are annealed, for example at ~250° C. for 30 minutes at $1.0 \times 10^{-2}$ Pascals, whiskers are produced.

Preferably, the whiskers are monocrystalline or polycrystalline rather than amorphous. The properties, both chemical and physical, of the layer of whiskers are anisotropic due to the crystalline nature and uniform orientation of the microstructures. Typically, orientation of the whiskers is uniformly perpendicular relative to the substrate surface. The preferred length of each whisker is in the range of 0.1 to 3 µm, more preferably in the range of 0.5 to 2.5 µm. The cross-sectional width of each whisker is preferably less than 0.1 µm. The whiskers preferably have a high aspect ratio, (i.e., length of whisker to diameter of whisker ratio is in the range from about 3:1 to about 100:1). The areal number densities of the conformally coated nanostructured elements are preferably in the range of $1-200/\mu^2$, preferably in the range of $5-50/\mu m^2$.

Furthermore, whether the nanostructured elements are uniaxially-oriented or randomly-oriented, it is preferred that at least one point of each nanostructured element contact a two-dimensional surface common to all of the nanostructured elements.

Referring to FIG. 1B, nanostructured elements (14), submicrometer in width and a few micrometers in length, are composites comprising the organic core whisker (12) and at least one conformal coating (13). Conformal coating materials are selected from the group consisting of biomaterials, organic materials, such as self-assembled monolayers, organic pigments, such as phthalocyanines or heterocyclic aromatic compounds, or an inorganic material. Generally the conformal coating material is selected to optimize biomolecule adsorption and binding. Preferably, the inorganic coating material is selected from the group consisting of conducting metals, semi-metals, dielectrics and semiconductors. Preferred metallic conformal coating materials include Pt, Pd, Ag, Cu, Au, and alloys, such as CrCo, NiCr, and PtIr. The wall thickness of the conformal coating material surrounding the whiskers is in the range from about 0.5 nm to about 50 nm.

The conformal coating may be deposited onto the whiskers using conventional techniques, including, for example, those described in U.S. Pat. No. 5,039,561. Preferably, the conformal coating is deposited by a method that avoids disturbance of the nanostructured surface region by mechanical or mechanical-like forces. More preferably, inorganic conformal coatings are deposited by vacuum deposition methods, such as, vacuum sublimation, sputtering, vapor transport, and chemical vapor deposition.

Additionally, a second, third or more conformal coating can be applied to the nanostructured elements. A particularly useful method of applying an additional conformal coating is by adsorption of an organic material from solution, for example, a thio-terminated oligomer.

Although multi-component nanostructured elements (such as those described above) are preferred, single component nanostructured elements are also contemplated by this invention. The single component elements have dimensions similar to the multicomponent elements, however, the single component elements consist only of a single material, such as a metal, as described above in reference to the metal conformal coating.

Optionally, although not preferred, an organic or inorganic encapsulant may be applied to the exposed surface of the nanostructured surface region, wherein the encapsulant wholly or partially encapsulates the nanostructured elements. The encapsulant may be applied from a liquid, vapor, or solid state to the nanostructured surface region by means appropriate for the particular encapsulant. The applied encapsulant may be solidified, condensed or polymerized by means appropriate to the particular material used.

After the nanostructured elements are encapsulated, the resulting composite article, that is, an encapsulated biological adsorption support of the present invention, is delaminated from the substrate at the substrate-nanostructured layer interface by mechanical means such as, for example, pulling the encapsulated biological adsorption support from the substrate, pulling the substrate from the encapsulated biological adsorption support, or both. In some instances, the encapsulated biological adsorption support may self-delaminate during solidification of the encapsulant.

An alternative and preferred process is a solventless process for fabricating the encapsulated biological adsorption support and is applicable in concept to any nanostructured surface component, that is, one comprising nanostructured elements of various material compositions, shapes, orientations, and packing densities. The nanostructured elements may be hot roll calendered into a polymer web to any predetermined depth, as described in U.S. Pat. No. 5,352,651.

Biological adsorption supports are produced in large area sheets, on substrates that are typically 25–50 µm thick, suitable for cutting or punching out many small sample pieces. For example, small diameter discs (~6 mm) may be punched out and placed in the bottom of microtitration wells such that the nanostructured surface faces the interior of the well.

Advantageously, the high surface area and small size scale of the nanostructured surfaces are not compromised by incorporation of chemical and biological functionality into the conformal coatings of the whiskers, thereby increasing the usefulness and specificity for biological activity of the nanostructured surfaces. We believe that the approximate order of magnitude increase of bound protein on the biological adsorption supports of the present invention results from the 10- to 15-fold increase in surface area of the nanostructured surfaces shown in the Examples.

The proportion of tightly bound biomolecules measured by SDS resistances is uniformly high, especially for Pt, and represents improvement over conventional supports. While not intending to be bound by theory and compared to conventional biological adsorption supports, the homogeneity of small scale hydrophobic and hydrophilic areas might be expected to be better on a naturally oxidized pure metal substrate, and explain in part the higher SDS resistances as well as the mass binding levels.

While not intending to be bound by theory, it is believed the ease with which charge can redistribute on a metal substrate (sorbent) compared to an insulating (polymer) material may also facilitate binding as a dissolved biomolecule approaches the sorbent-water interface where dispersion and electrostatic image forces occur. The effective entrapment of the biomolecule between relatively tall columnar whiskers as they diffuse to and from the sorbent, should give rise to many more biomolecule/sorbent collisions per unit random-walk-distance than would occur over a uniformly flat sorbent surface. That is, if a biomolecule approaches a whisker surface, but does not adsorb, diffusing away instead, it will predominantly be heading towards another whisker surface, just a few "Fickian diffusion steps" away, because most of the whiskered surface area is on the sides of the whiskers. Over a non-structured, flat substrate, biomolecules statistically diffuse away half of the time. This collison rate enhancement may explain the improved kinetics of the adsorption process.

The biological adsorption support of the present invention may be used wherever the binding of biomolecules is useful. The supports are particularly advantageous where it is necessary to have biomolecules bound more tightly, or at a greater density, or at a greater rate of adsorption; for example, where the amount of bound biomolecules limits a reaction rate. Such situations typically occur in enzyme reactors, where generally, the reaction rate is first order in enzyme concentration. Another example is purification systems where the capacity of the system is typically proportional to the amount of some functionality, such as a bound biomolecule in an affinity purification system. Another example is an analytical test wherein the sensitivity of the test is proportional to the amount of detector molecule (ligand) sensitivity and is often limited by the number of detector molecules. If the density of bound detector molecules (often a biomolecule) is increased, the amount of bound analyte increases, thus the signal increases. Yet another example is the use of bound biomolecules as biosensors where the detection sensitivity is a function of the number of bound biomolecules.

Objects and advantages of this invention are further illustrated by the following examples, but the particular materials and amounts thereof recited in these examples, as well as the conditions and details, should not be construed to unduly limit this invention. All materials are commercially available or known in the art except where stated or otherwise apparent. All samples, unless otherwise stated were prepared and analyzed in triplicate and the averages along with the standard deviation are summarized and reported in the following tables.

EXAMPLES

SDS Resistance

The percent SDS resistance as reported below is calculated as follows:

[[tightly bound protein]÷[initially bound protein]]×100=% SDS Resistance. This is the percentage of the protein that resists solubilization by SDS treatment.

Examples 1–2

A glass microscope slide, 3 cm×10 cm, was rf sputter-coated with Cu to a thickness of about 100 nm. The organic pigment N,N'-di(3,5-xylyl)perylene-3,4:9,10 bis (dicarboximide)(PR149), was vacuum-vapor deposited (base pressure of about $2.0 \times 10^{-4}$ Pascals) onto the copper-coated microscope slide to a thickness of 146 nm at an average deposition rate of 20 m/min. The slide with the organic pigment layer was then vacuum annealed to a maximum temperature of 200° C. to convert the organic pigment layer to a nanostructured layer of discrete, perpendicularly oriented crystalline whiskers, as described in U.S. Pat. No. 4,812,352.

Approximately one-half of the whiskered organic pigment layer was then rf-sputter coated with copper to provide a conformal coating on the whiskers having a planar equivalent thickness of about 100 nm. The effective thickness of the copper coating was significantly less than 100 nm due to the much larger surface area of the whiskers relative to a flat surface. Approximately one-third of the whiskers was sputter-coated with platinum to provide a conformal platinum coating having an equivalent planar thickness of about 100 nanometers. The remaining approximately one-sixth of the slide area was left as prepared above with bare PR149 whiskers.

A conventional air pressurized paint sprayer was used to spray a layer of an encapsulating Latex precursor (commercially available under the trade designation "STRIPPABLE MASKANT YR-43" from 3M Co.) over the conformal coated nanostructured layer to provide a wet thickness of about 0.157 to 0.165 min. The encapsulating layer was then dried in a conventional air oven at a temperature of about 66° C. for approximately 20 minutes.

Sets of three 5 mm square samples were cut from each of the three regions of the composite coated article, and peeled off the glass slide with tweezers. The original Cu coating on the glass slide remained on the slide. The first sample set contained Cu-conformally coated whiskers, encapsulated in the strippable maskant (Example 1). The second set of three samples contained Pt-conformally coated whiskers, encapsulated in the strippable maskant (Example 2). A first control was a set of 5 mm squares containing bare whiskers (not conformally coated) encapsulated in the strippable maskant. As a second control, a set of three 5 mm squares were cut from a dried layer of the strippable maskant which had been sprayed on a steel plate, producing a surface with no encapsulated nanostructure.

Figure 2:
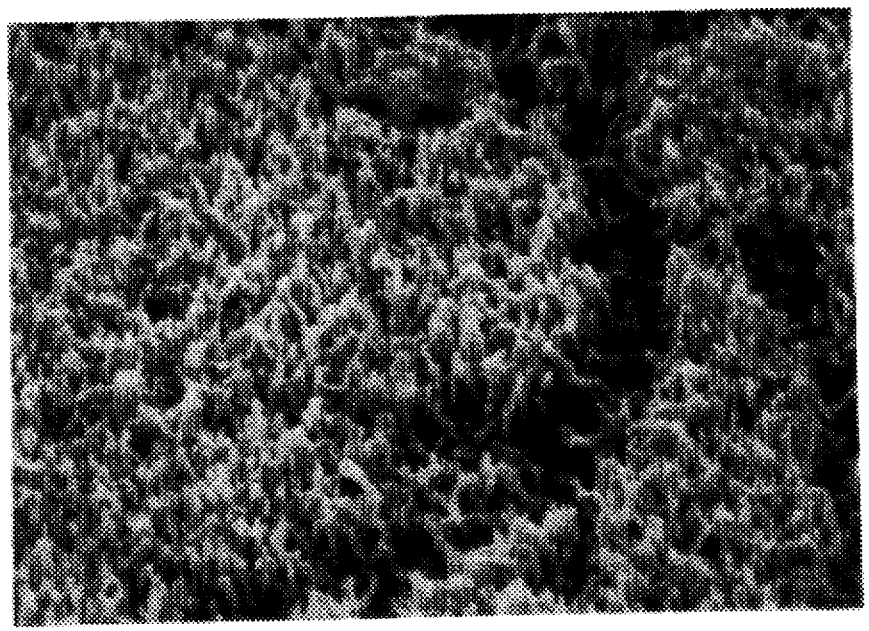
FIG. 2 is a scanning electron micrograph (SEM) of latex partially-encapsulated, Pt-coated whiskers forming a nanostructured elements for Protein A adsorption, magnification 10,000.

The nanostructured surfaces of the sample pieces having the metal coated whiskers appeared very black due to their high light trapping efficiency. The surface of the Pt-conformally coated whiskers partially embedded in the strippable maskant appeared more textured than that of the Cu-conformally coated whiskers and is respresented in the SEM photograph of FIG. 2.

For protein binding measurements, each individual sample square was incubated with rocking for 18 hours in 250 μg/mL, $^{125}$I-radiolabeled solution of Protein A (Genzyme Corp., Boston, Mass.) in phosphate-buffered saline (0.15M NaCl in 25 mM sodium phosphate), hereinafter referred to as PBS, pH 7.5 J. Chromatog., vol. 512, p. 345–363 (1990) Surfaces were then treated with 3.0M ethanolamine, pH 9.0 for 1 hour, and given four rinses in PBS. The initial bound protein level was determined by measuring the residual radioactivity in a Packard auto-gamma radiation counter Model 5230 (Canberra Industries Inc./Packard Instrument Co., Meriden, Conn.) Each set of samples, Pt-coated, Cu-coated and uncoated were prepared and analyzed in triplicate. A latex control was also prepared and analyzed in triplicate. Sample averages and mean deviations of protein mass per unit area uptake for the three uncoated, Pt and Cu conformally-coated whisker samples, as well as the latex control are summarized in Table 1.

The samples were then further incubated for 4 hours at 37° C. in a 1% aqueous solution of SDS, followed by rinsing three times with SDS, to remove loosely-bound protein. The remaining radioactivity was measured again to determine the residual tightly bound protein. The triple sample averages and mean deviations of SDS resistance and the tightly bound protein density are summarized in Table 1.

Notably, the Pt-conformally coated whisker sample had significantly higher binding and SDS resistance Compared to the other sample types.

Although the latex control samples and the Cu-coated whiskers samples were torn and the uncoated samples were broken up after the SDS treatment, samples were subjected to analytical treatment and are reported in Table 1. The Pt-conformally coated whiskers appeared to remain intact.

TABLE 1

| Sample | Initial Binding (μg/cm$^2$) | Tightly Bound (μg/cm$^2$) | SDS Resistance (%) |
| --- | --- | --- | --- |
| Latex (control) | 0.63 ± 0.06 | 0.06 ± 0.01 | 9.0 ± 1.7 |
| Bare Whisker (control) | 0.65 ± 0.10 | 0.15 ± 0.06 | 22.8 ± 6.5 |
| Cu/Whisker (Example 1) | 0.79 ± 0.11 | 0.29 ± 0.02 | 37.8 ± 6.8 |
| Pt/Whisker (Example 2) | 3.46 ± 0.52 | 2.69 ± 0.37 | 77.6 ± 2.3 |

Examples 3–4

These examples used the same partially encapsulated nanostructured sample types as prepared in Examples 1 and 2, but used shorter incubation times and different buffer solutions.

Sample squares, 5 mm on a side, were cut from the latex encapsulated whiskered sample prepared as described in Examples 1 and 2 and delaminated from the Cu-coated glass slide. Six squares were cut from each of the Pt and Cu coated areas, and the plain latex control. Only three samples were available from the bare whiskered control area. The same Protein A binding process and measurement as described in Examples 1 and 2 was used except the initial protein incubation period was 2 hours instead of 18 hours, and two different buffer solutions were tested. Three sample squares of each type were coated with Protein A in PBS at pH 7.5, and the other three squares coated with Protein A in 1.5 molar sodium sulfate in sodium phosphate buffer, hereinafter referred to as "sulfate buffer," at pH 7.5. The three 5 mm squares from the encapsulated bare whisker sample area were coated only with Protein A in the PBS buffer. All samples were rinsed three times with the PBS buffer after inactivation with ethanolamine.

Table 2 summarizes the initial binding, SDS resistance and tightly bound protein densities for the triplicate samples with standard deviations, for each sample type and buffer condition. The results in Table 2 corroborate the results in Examples 1 and 2, that the Pt-coated samples show considerably better protein adsorption than either the Cu-coated or bare whisker types, and continue the trend of very high SDS resistance. For Pt, the sulfate buffer produced more bound protein.

TABLE 2a (PBS)

| Ex. | Support | Initial Binding (μg/cm$^2$) | Tightly Bound (μg/cm$^2$) | SDS Resistance (%) |
| --- | --- | --- | --- | --- |
| Ctrl | Latex | 0.113 ± 0.005 | 0.023 ± 0.003 | 20.3 ± 1.9 |
| Ctrl | Bare whiskers | 0.111 ± 0.007 | 0.022 ± 0.002 | 20.2 ± 0.2 |
| 3 | Cu/Whiskers | 0.172 ± 0.014 | 0.078 ± 0.006 | 45.6 ± 0.6 |
| 4 | Pt/Whiskers | 0.303 ± 0.010 | 0.214 ± 0.018 | 70.5 ± 3.7 |

TABLE 2b (Sodium Sulfate)

| Ex. | Support | Initial Binding (μg/cm$^2$) | Tightly Bound (μg/cm$^2$) | SDS Resistance (%) |
| --- | --- | --- | --- | --- |
| Ctrl | Latex | 0.145 ± 0.005 | 0.036 ± 0.003 | 25.1 ± 1.0 |
| Ctrl | Bare whiskers | N.A. | N.A. | N.A. |
| 3 | Cu/Whiskers | 0.148 ± 0.017 | 0.06 ± 0.012 | 40.2 ± 3.1 |
| 4 | Pt/Whiskers | 0.456 ± 0.005 | 0.368 ± 0.009 | 80.8 ± 2.3 |

Examples 5–8

Examples 5–8 demonstrate that the nanostructured surface area of non-encapsulated whiskers adsorb far larger quantities of protein in much shorter exposure times, and reveal the relative effect of the various metals, independent of the surface morphology.

Figure 3:
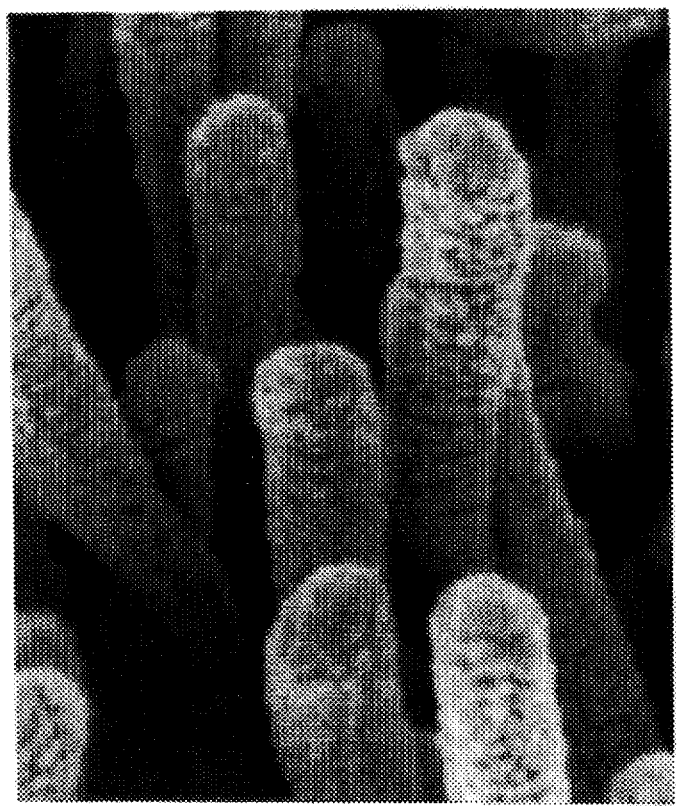
FIG. 3 is an SEM of nonencapsulated, Pt-coated whiskers, grown on a Cu-coated polymide substrate, magnification 150,000.

These examples specifically compare four different metal types, all coated onto different quadrants of the same sample, thus assuring the whisker microstructure was identical for each. Although specific to Examples 9–12, FIG. 3 shows an SEM micrograph of Pt-conformally coated whiskers, typical of those used in this example.

A polyimide sheet 0.050 mm (2 mil) thick (ICI Films) was stretch-mounted between two stainless steel rings to form a disc 8.3 cm in diameter. Copper was rf sputter coated onto this polyimide substrate disc to an approximate thickness of 180 nm. PR149 red pigment was vacuum vapor deposited onto the copper-coated polyimide as described in Examples 1–2, to an approximate thickness of 150 nm and annealed in vacuum (base pressure $2.5 \times 10^{-5}$ Pascals) at a temperature of 280° C. for 40 minutes. The red pigment coated polyimide was converted into the 1–2 µm tall oriented crystalline whiskers.

In a separate conventional (13.47 MHz) rf sputter vacuum chamber, the whiskers were conformally coated by sequentially sputter depositing Cu (Example 5), CoCr (86:14) (Example 6), and Fe (Example 7) separately onto each of three quadrants, through a metal mask exposing only one quadrant of the substrate disc at a time. The 20 cm target was 10 cm above the sample, the substrate was water-cooled and the sputtering was done in 3.2 Pascals of Ar at 500 Watts forward power and 1200–1600 volts target bias for 10 minutes. The mass equivalent thickness of the Cu, CoCr and Fe were, respectively, approximately 350 nm, 250 nm and 250 nm. In a separate, similar sputtering chamber, Pt was sputtered to a mass equivalent thickness of 120 nm onto the fourth quadrant of the disc (Example 8).

As a control, a second Cu-coated polyimide disc was vapor coated with PR149, but not annealed (that is, there were no whiskers). Fe, Cu, CoCr and Pt coatings were sputter deposited onto this unconverted pigment layer in the same manner as for Examples 5–8.

Six squares, 5 mm on a side, were cut from each quadrant of the nanostructured sample disc and the control sample disc (for a total 48 squares). The squares were incubated, in triplicate, in 250 µg/ml $^{125}$I-Protein A solution in either PBS or sulfate buffer, for two hours without vortexing or rocking. All the samples were rinsed in the appropriate buffer. Residual unoccupied surfaces were passivated with a non-radiolabeled BSA (bovine serum albumin) solution (2.5 mg/mL in the PBS buffer) by incubating or reacting without rocking or vortexing for 1 hour.

After three rinses with the PBS buffer solution, the total bound Protein A was determined from the remaining radioactivity, as described in Examples 1–2. SDS treatment, as described in Example 1, without rocking, was then used to remove loosely-bound protein. The radioactivity measurements were repeated to determine the tightly bound protein densities.

Table 3 summarizes for each buffer solution the initial binding, SDS resistance, and tightly bound protein mass for the four metal-coated whisker sample types. No data were obtained from the control samples since all the metal coated PR 149 reference samples, which did not have the whisker structure, fell apart after the rinses or SDS treatment. That is, the perylene coating with its metal overlayer delaminated from the polyimide substrate. All the metal-coated whiskered samples remained intact throughout the experiment.

TABLE 3a (PBS)

| Ex. | Support | Initial Binding (µg/cm$^2$) | Tightly Bound (µg/cm$^2$) | SDS Resistance (%) |
|---|---|---|---|---|
| 5 | Fe/Whiskers | 2.86 ± 0.10 | 2.30 ± 0.05 | 80 ± 2 |
| 6 | CoCr/Whiskers | 3.35 ± 0.68 | 2.55 ± 0.42 | 77 ± 3 |
| 7 | Cu/Whiskers | 6.43 ± 0.29 | 4.36 ± 0.40 | 68 ± 9 |
| 8 | Pt/Whiskers | 7.52 ± 0.26 | 6.94 ± 0.18 | 92 ± 2 |

TABLE 3b (Sulfate Buffer)

| Ex. | Support | Initial Binding (µg/cm$^2$) | Tightly Bound (µg/cm$^2$) | SDS Resistance (%) |
|---|---|---|---|---|
| 5 | Fe/Whiskers | 5.19 ± 0.99 | 3.79 ± 0.40 | 74 ± 8 |
| 6 | CoCr/Whiskers | 4.62 ± 0.34 | 3.64 ± 0.14 | 79 ± 4 |
| 7 | Cu/Whiskers | 10.91 ± 0.68 | 6.84 ± 0.95 | 62 ± 7 |
| 8 | Pt/Whiskers | 10.24 ± 0.41 | 9.64 ± 0.50 | 94 ± 2 |

The results in Tables 3a and 3b show exceptionally high mass densities of Protein A were tightly adsorbed on the nonencapsulated, metal coated whiskers in only two hours, without rocking or vortexing the samples at any stage. These quantities were an order of magnitude greater than obtained with the encapsulated whiskers in Examples 3–4.

Examples 9–14

These examples examine the kinetics of adsorption on non-encapsulated, Pt-conformally coated whiskers, showing that incubation times as short as 7.5 minutes are sufficient for significant binding, and also include two additional proteins, BSA and human IgG antibody.

An 8.3 cm diameter disc of copper coated polyimide was vapor coated with PR149 and annealed as described in Examples 3–8. The resulting nanostructured whiskers were conformally coated with Pt to a mass equivalent thickness of 120 nm, as described in Examples 5–8, using an rf sputtering pressure of 1.3 Pascals of Ar and 200 Watts forward power. FIG. 3 shows a high resolution SEM micrograph of the Pt coated whiskers, at 150,000 magnification. A high level of very fine nodular structure is clearly apparent in the Pt-coating on the whiskers.

Sufficient numbers of 5 mm square sample pieces were cut from the disc to perform binding studies, in triplicate, for three proteins, (Protein A, human IgG antibody and BSA), in both PBS and sulfate buffer systems, for five incubation times, 7.5, 15, 30, 60 and 120 minutes. $^{125}$I-Protein A solutions were the same as used in Examples 1–8. The concentrations of all three proteins was 250 µg/mL (BSA and human IgG are both commercially available from Sigma Chemical Co. in the non-radioactive form).

The chloride concentration was 0.15M, pH 7.5, for all three proteins. The sulfate concentration was 1.5M, pH 7.5 for Protein A and BSA, and 0.75M, pH 7.5 for human IgG.

All unreacted binding sites were inactivated with non-radiolabeled BSA solution (2.5 mg/mL) for one hour followed by rinsing with PBS three times, once for 30 minutes and twice for 10 minutes. SDS treatment described in Example 1 was used to denature and to remove any loosely bound protein. Finally, an identical set of control samples was run using the plain, uncoated polyimide film.

Figure 4:
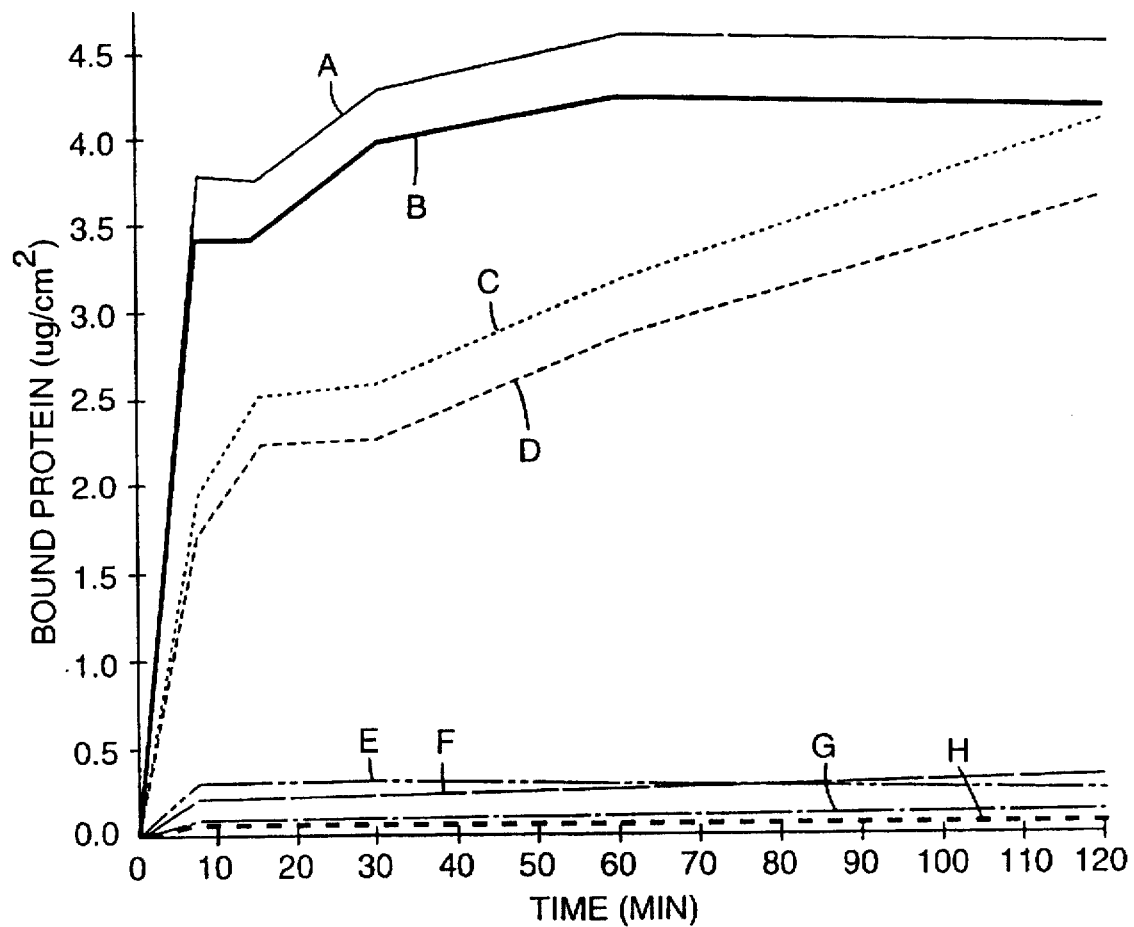
FIG. 4 is a graphical representation of initial and tightly bound Protein A mass adsorbed as a function of time.
Figure 5:
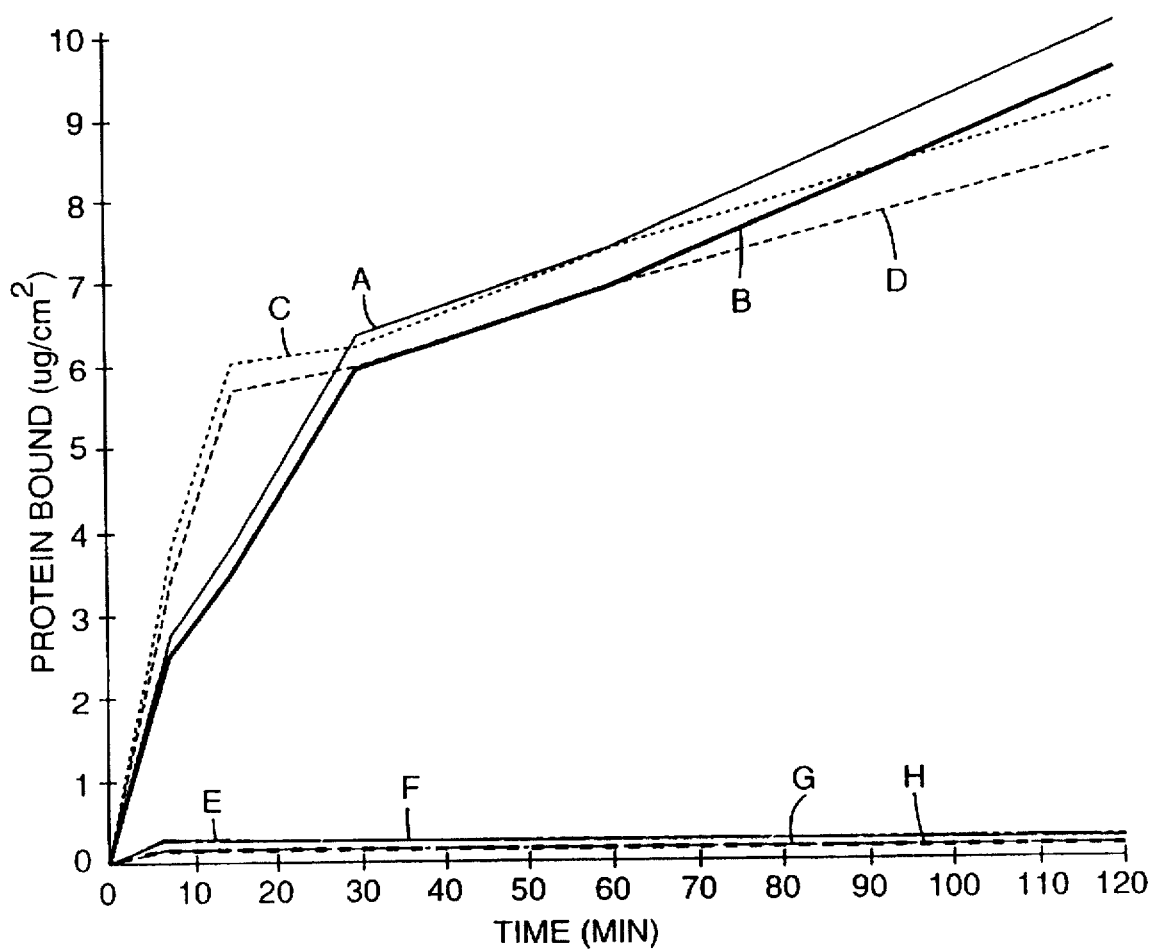
FIG. 5 is a graphical representation of initial and tightly bound bovine serum albumin (BSA) mass adsorbed as a function of time.
Figure 6:
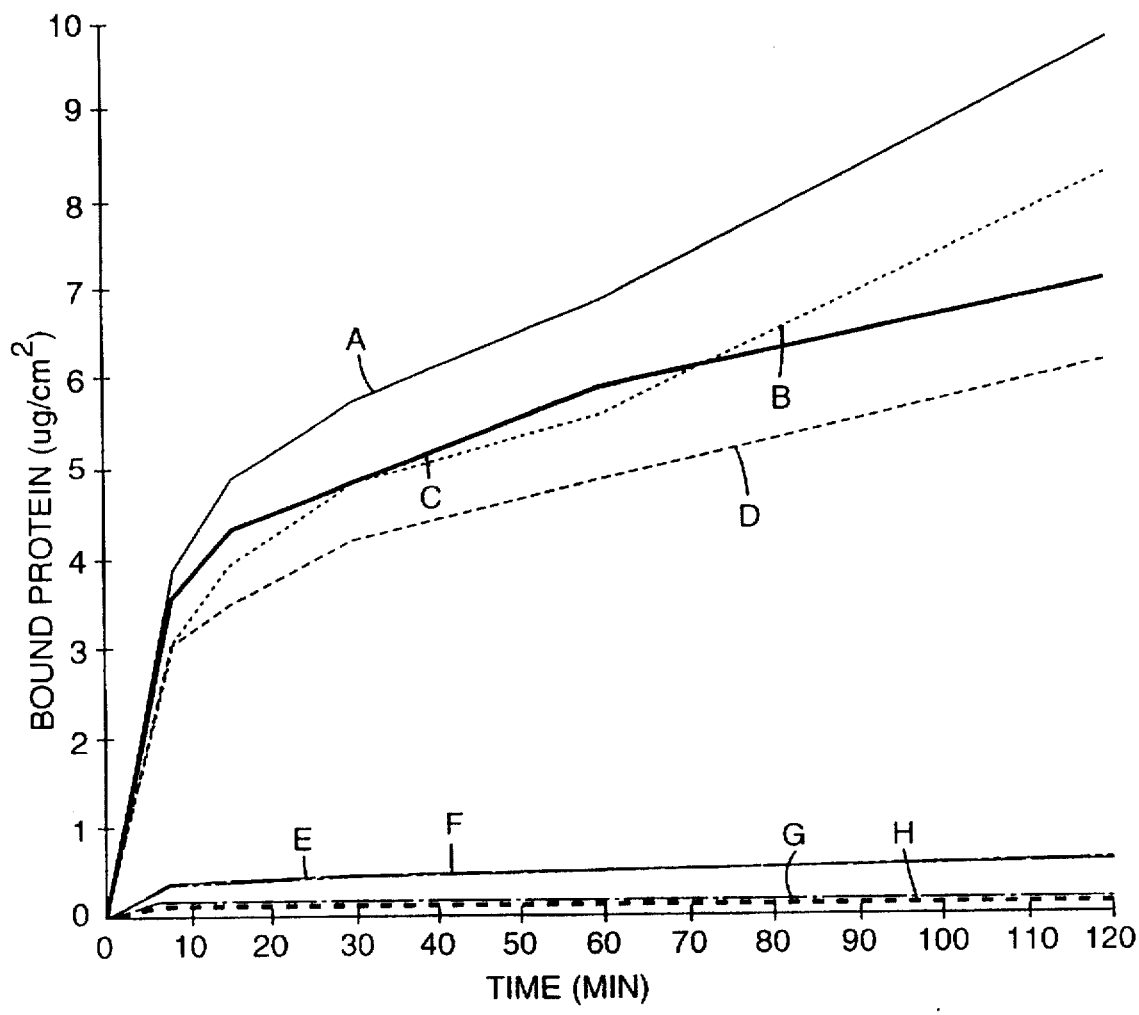
FIG. 6 is a graphical representation of initial and tightly bound human immunoglobulin G (IgG) mass adsorbed as a function of time.

Tables 4 and 6 summarize the initial binding mass densities, SDS resistance and tightly bound mass densities, with standard deviations for the triplicate measurements, listed according to protein type and exposure time, for the two buffer systems, respectively. Tables 5 and 7 summarize the initial binding mass densities, SDS resistance and tightly bound mass densities from the bare polyimide controls for the three proteins and two buffer solutions, as a function of time. FIGS. 4–6 (curves A–D) are graphs of the initial and tightly bound protein, respectively, as a function of adsorption time for the two buffers.

A PBS
B PBS (post-SDS)
C sulfate buffer
D sulfate buffer (post-SDS)
E control in sulfate buffer
F control in PBS
G control in PBS (post-SDS)
H control in sulfate buffer (post-SDS)

First, the binding levels are again very high, consistent with Examples 5–8, and higher for hIgG and BSA than Protein A. Second, the binding levels are nearly plateaued by 15 minutes, and may be significantly high at times less than the minimum observed 7.5 minutes. Third, in contrast to Examples 5–8, the binding levels in PBS are higher than those in the sulfate buffer for human IgG (hIgG) and Protein A. Fourth, the SDS resistances are again very high and remarkably uniform.

TABLE 4

Summary of the average and standard deviation of protein binding and SDS resistance on Pt-coated whiskers as a function of exposure time for each of three proteins, in PBS.

| Protein (Examples 9–11) PBS | Time (min.) | Initial Binding ($\mu g/cm^2$) | Tightly Bound ($\mu g/cm^2$) | SDS Resistance (%) |
|---|---|---|---|---|
| Protein A | 7.5 | 3.77 ± 0.29 | 3.44 ± 0.20 | 91 ± 2 |
| ' | 15.0 | 3.75 ± 0.32 | 3.43 ± 0.22 | 92 ± 3 |
| ' | 30.0 | 4.26 ± 0.33 | 3.98 ± 0.27 | 93 ± 2 |
| ' | 60.0 | 4.57 ± 0.06 | 4.23 ± 0.10 | 92 ± 2 |
| ' | 120.0 | 4.50 ± 0.34 | 4.15 ± 0.35 | 92 ± 1 |
| human IgG | 8.0 | 3.84 ± 0.4 | 3.07 ± 0.20 | 80 ± 5 |
| ' | 15.0 | 4.86 ± 0.22 | 3.88 ± 0.26 | 80 ± 4 |
| ' | 30.0 | 5.69 ± 0.66 | 4.81 ± 0.60 | 84 ± 1 |
| ' | 60.0 | 6.80 ± 0.51 | 5.52 ± 0.53 | 81 ± 3 |
| ' | 120.0 | 9.67 ± 1.16 | 8.15 ± 0.57 | 85 ± 6 |
| BSA | 7.5 | 2.75 ± 0.07 | 2.55 ± 0.09 | 93 ± 1 |
| ' | 15.0 | 3.84 ± 0.42 | 3.54 ± 0.40 | 92 ± 1 |
| ' | 30.0 | 6.37 ± 0.46 | 5.98 ± 0.40 | 94 ± 1 |
| ' | 60.0 | 7.34 ± 0.34 | 6.94 ± 0.24 | 95 ± 1 |
| ' | 120.0 | 10.03 ± 0.31 | 9.48 ± 0.26 | 94 ± 1 |

TABLE 5

Summary of the average and standard deviation of protein binding and SDS resistance of polyimide film control samples as a function of exposure time, for 3 proteins in PBS.

| Protein (Examples 9–11) Control/PBS | Time (min.) | Initial Binding ($\mu g/cm^2$) | Tightly Bound ($\mu g/cm^2$) | SDS Resistance (%) |
|---|---|---|---|---|
| Protein A | 7.5 | 0.44 ± 0.02 | 0.16 ± 0.01 | 34 ± 2 |
| " | 30.0 | 0.48 ± 0.02 | 0.18 ± 0.02 | 35 ± 3 |
| " | 120.0 | 0.64 ± 0.04 | 0.24 ± 0.01 | 37 ± 1 |
| human IgG | 7.5 | 0.78 ± 0.04 | 0.28 ± 0.01 | 36 ± 3 |
| " | 15.0 | 0.78 ± 0.04 | 0.30 ± 0.01 | 38 ± 2 |
| " | 30.0 | 0.94 ± 0.08 | 0.36 ± 0.03 | 37 ± 2 |
| " | 60.0 | 1.02 ± 0.06 | 0.38 ± 0.01 | 37 ± 2 |
| " | 120.0 | 1.04 ± 0.03 | 0.42 ± 0.02 | 36 ± 1 |
| BSA | 7.5 | 0.50 ± 0.07 | 0.26 ± 0.03 | 50 ± 3 |
| " | 30.0 | 0.42 ± 0.03 | 0.22 ± 0.02 | 50 ± 1 |
| " | 120.0 | 0.48 ± 0.03 | 0.26 ± 0.02 | 51 ± 3 |

Such comparatively very low values of protein uptake on planar polymer surfaces are further exemplified by the results from the plain, uncoated polyimide control samples. The average tightly bound protein amounts from the control samples (curves E–H) are also plotted in FIGS. 4–6, where it is shown that the nanostructured fills adsorb up to 70 times as much protein in two hours as the bare polyimide.

TABLE 6

Summary of the average and standard deviation of protein binding and SDS resistance on the Pt coated whiskers as a function of exposure time for three proteins in sulfate buffer.

| Protein (Examples 12–14) Sulfate Buffer | Time (min.) | Initial Binding ($\mu g/cm^2$) | Tightly Bound ($\mu g/cm^2$) | SDS Resistance (%) |
|---|---|---|---|---|
| Protein A | 7.5 | 1.96 ± 0.05 | 1.71 ± 0.10 | 87 ± 3 |
| ' | 15.0 | 2.51 ± 0.25 | 2.23 ± 0.21 | 89 ± 2 |
| ' | 30.0 | 2.58 ± 0.11 | 2.27 ± 0.06 | 88 ± 2 |
| ' | 60.0 | 3.16 ± 0.32 | 2.84 ± 0.19 | 90 ± 4 |
| ' | 120.0 | 4.06 ± 0.04 | 3.60 ± 0.04 | 89 ± 2 |
| human IgG | 8.0 | 3.48 ± 0.14 | 2.99 ± 0.14 | 86 ± 3 |
| ' | 15.0 | 4.30 ± 0.64 | 3.45 ± 0.40 | 81 ± 2 |
| ' | 30.0 | 4.83 ± 0.69 | 4.14 ± 0.60 | 86 ± 4 |
| ' | 60.0 | 5.85 ± 0.96 | 4.84 ± 0.90 | 82 ± 2 |
| ' | 120.0 | 7.02 ± 0.74 | 6.09 ± 0.95 | 86 ± 5 |
| BSA | 7.5 | 3.77 ± 0.38 | 3.43 ± 0.29 | 91 ± 2 |
| ' | 15.0 | 6.01 ± 0.12 | 5.66 ± 0.06 | 95 ± 1 |
| ' | 30.0 | 6.21 ± 0.37 | 5.91 ± 0.30 | 95 ± 1 |
| ' | 60.0 | 7.36 ± 0.11 | 6.94 ± 0.01 | 94 ± 2 |
| ' | 120.0 | 9.08 ± 1.84 | 8.47 ± 2.05 | 92 ± 4 |

TABLE 7

Summary of the average and standard deviation of protein binding and SDS resistance of polyimide film control samples as a function of exposure time for three proteins in sulfate buffer.

| Protein (Examples 12–14) Control/Sulfate Buffer | Time (min.) | Initial Binding ($\mu g/cm^2$) | Tightly Bound ($\mu g/cm^2$) | SDS Resistance (%) |
|---|---|---|---|---|
| Protein A | 7.5 | 0.28 ± 0.09 | 0.06 ± 0.02 | 19 ± 1 |
| ' | 30.0 | 0.30 ± 0.04 | 0.06 ± 0.01 | 21 ± 2 |
| ' | 120.0 | 0.24 ± 0.09 | 0.07 ± 0.01 | 27 ± 2 |
| human IgG | 7.5 | 0.35 ± 0.04 | 0.14 ± 0.02 | 40 ± 2 |
| ' | 15.0 | 0.35 ± 0.04 | 0.14 ± 0.02 | 39 ± 1 |
| ' | 30.0 | 0.42 ± 0.02 | 0.16 ± 0.02 | 38 ± 2 |
| ' | 60.0 | 0.51 ± 0.05 | 0.18 ± 0.02 | 35 ± 2 |
| ' | 120.0 | 0.52 ± 0.07 | 0.17 ± 0.02 | 32 ± 2 |
| BSA | 7.5 | 0.22 ± 0.04 | 0.11 ± 0.02 | 47 ± 1 |
| ' | 30.0 | 0.24 ± 0.05 | 0.11 ± 0.02 | 46 ± 1 |
| ' | 120.0 | 0.28 ± 0.02 | 0.13 ± 0.01 | 46 ± 3 |

Example 15

Figure 7:
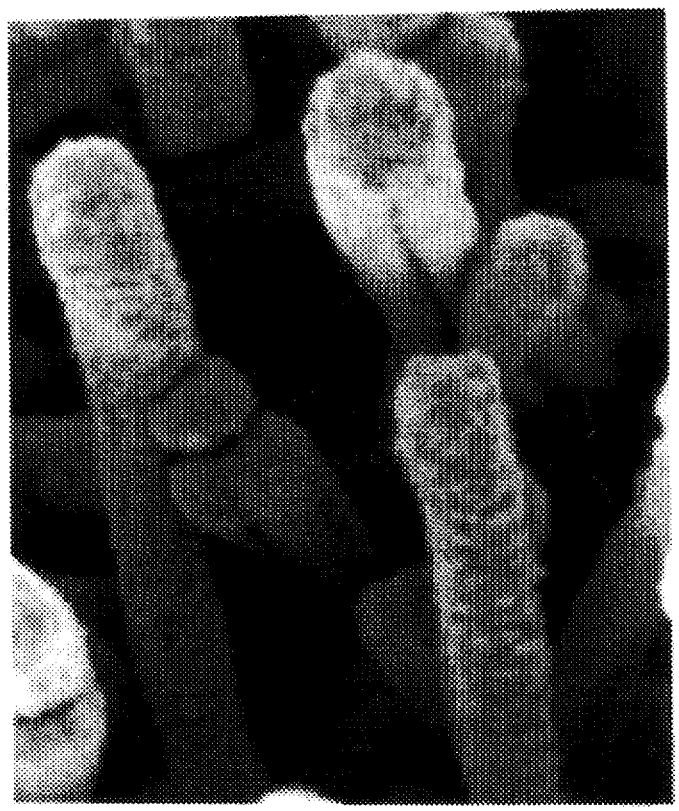
FIG. 7 is an SEM of Pt-coated whiskers after the adsorption of Protein A, magnification 150,000.

For comparison to FIG. 3, taken before any protein adsorption, FIG. 7 shows a high resolution scanning electron micrograph, 150,000 magnification, of the same Pt-coated whisker sample after adsorption of Protein A (250 μg/mL) in PBS for 1 hour, without rocking, followed by three 10 minute rinses in water.

The same ultrafine texture was seen in the Pt conformal coating on the whiskers as in FIG. 3, but the texture was not as visually sharp or distinct, as though the resolution was degraded. The secondary electron emission was not as high from the protein-coated Pt whiskers in FIG. 7, that is, they did not appear as bright in general as the nonexposed whiskers. These observations are consistent with a secondary nonconductive coating over the Pt, such as protein molecules, which were nestled into the nooks and crannies of the overtly bumpy surface texture of sputtered Pt. This difference in appearance of the roughness of the Pt coating on the nonexposed and protein exposed whiskers is seen on all the whiskers, that is, the micrographs in FIGS. 3 and 7 are not unique.

Example 16

This example demonstrates that protein bound to nanostructured films retains its biological activity and is useful as a protein adsorption support.

An 8.3 cm diameter disc of copper coated 0.050 mm thick polyimide was vapor coated with PR149 and annealed as described in Examples 9–14. The resulting nanostructured whiskers were conformally coated with Pt to a mass equivalent thickness of 120 nm, again as described in Examples 9–14, using an rf sputtering pressure of 1.3 Pascals of Ar and 200 Watts forward power. FIG. 3 shows a high resolution SEM micrograph of the Pt coated whiskers. Two identical sets of three 5 mm square pieces were cut from the nanostructured sample disc and an uncoated polyimide control film respectively. One set (Set I) was reacted with 300 µL of a $^{125}$I Protein A at a concentration of 250 µg/mL in PBS, pH 7.5 for 60 minutes at ambient temperature. At the same time the second set (Set II) was reacted with an identical but unlabeled Protein A solution under identical conditions. Both sets were then treated with 500 µL of 2.5 mg/mL BSA in PBS, pH 7.5, for 19 hours at ambient temperature. The lengthened time was necessary to insure complete blocking of the surface. As in earlier examples no vortexing or rocking was done, only gentle swirling until the sample was immersed. Both sets were rinsed four times with 500 µL of purified water (available from Millipore under the commercial tradename Milli-Q water) for 15 minutes each. Set I was measured for radioactivity while Set II was dried for 5 hours in an ambient vacuum oven. Set II was incubated with 300 µL of a 250 µg/mL $^{125}$I-human IgG in PBS, pH 7.5, at ambient temperature for 18 hours. This set was then rinsed four times with 500 µL PBS for 15 minutes each prior to radioactive determination.

Table 8 summarizes the amount of Protein A bound to the surfaces, the ratio of antibody bound per Protein A bound, and the amount of antibody bound per unit surface area.

TABLE 8

Summary of the binding of human IgG antibody to Protein A which was immobilized on the Pt coated nanostructured whiskers.

| Sample Type | Bound Protein A (µg/cm$^2$) | Bound hIgG (µg/cm$^2$) | hIgG/Protein A ratio | hIgG (µmoles/cm$^2$) |
|---|---|---|---|---|
| Nanostructured | 5.75 ± 0.38 | 25.9 ± 11.5 | 1.34 | 1.72 × 10−4 |
| Control | 0.12 ± 0.01 | 0.79 ± 0.17 | 1.95 | 0.05 × 10−4 |

Table 8 shows a fifty-fold greater Protein A binding to the nanostructured surface than to the polyimide control film per unit area. The amount of human IgG that binds was increased 33-fold, indicating a substantial retention of its biological activity. The results demonstrated that the nanostructured surfaces can be usefully employed to purify IgG from a solution and concentrate it onto a solid support.

Various modifications and alterations of this invention will become apparent to those skilled in the art without departing from the scope and spirit of this invention, and it should be understood that this invention is not to be unduly limited to the illustrative embodiments set forth herein above.

What is claimed:

1. A method of using a biological adsorption support comprising the steps of passing a fluid stream containing a biologically active material over the biological adsorption support and separating the biologically active material from the fluid stream, wherein the biological adsorption support comprises an inert substrate supporting a nanostructured surface comprising metal-coated, discrete nanostructured elements having an areal number density in the range of 1–200 µm$^2$.

2. The method according to claim 1 wherein each of the nanostructured elements is a two-component elements wherein the first component is an oriented whisker and a second component is biomolecule adsorbent conformal coating, such that the conformal coating coats the first component.

3. The method according to claim 1 wherein a biologically active material is adsorbed onto the biological adsorption support.

4. The method according to claim 1 wherein the nanostructured elements have an aspect ratio of greater than 3.

5. A composite article comprising
   (a) a biological adsorption support comprising of an inert substrate supporting a nanostructured surface comprising biomolecule adsorbent conformal-coated, oriented, discrete submicron-size elements having an areal number density in the range of 1–200/µm$^2$ and
   (b) a monolayer of biologically active material adhered to the biomolecule adsorbent conformal-coated elements, wherein the adhered layer is biologically active.

6. The composite article according to claim 5 wherein the biomolecule adsorbent conformal coating is a noble metal.

7. A method of using the composite article according to claim 5 as at least one of a separation device, a sensor, for immunoassay, an extraction device, or as a filter.

8. A composite article comprising:
   (a) a biological adsorption support, comprised of an inert substrate supporting a nanostructured surface comprising biomolecule absorbent conformal-coated, oriented, discrete submicron-size elements having an areal number density in the range of 1–200/µm$^2$,
   (b) a first monolayer of biologically active material adhered to the biomolecule absorbent conformal-coated elements, wherein the adhered layer is biologically active, and
   (c) a second monolayer of biologically active material adhered to the first monolayer of biologically active material.

9. A method of using the composite article according to claim 8 comprising the steps of passing a fluid stream containing a biologically active material over the biological adsorption support and separating the biologically active material from the fluid stream.

10. A method of using the composite article according to claim 8 comprising the steps of passing a fluid stream containing a biologically active material over the biological adsorption support and sensing the biologically active material in the fluid stream.

11. A method of using the composite article according to claim 8 comprising the steps of passing a fluid stream containing a biologically active material over the biological adsorption support and immunoassaying the biologically active material from the fluid stream.

12. A method of using the composite article according to claim 8 comprising the steps of passing a fluid stream containing a biologically active material over the biological adsorption support and extracting the biologically active material from the fluid stream.

13. A method of using the composite article according to claim 8 comprising the steps of passing a fluid stream containing a biologically active material over the biological adsorption support and filtering the biologically active material from the fluid stream.

* * * * *